(12) United States Patent
Cho et al.

(10) Patent No.: US 10,941,049 B2
(45) Date of Patent: Mar. 9, 2021

(54) WATER PURIFIER

(71) Applicant: LG INNOTEK CO., LTD., Seoul (KR)

(72) Inventors: Hyun Kyong Cho, Seoul (KR); Sung Won Roh, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 281 days.

(21) Appl. No.: 15/735,528

(22) PCT Filed: Jan. 6, 2016

(86) PCT No.: PCT/KR2016/000092
§ 371 (c)(1),
(2) Date: Dec. 11, 2017

(87) PCT Pub. No.: WO2016/200004
PCT Pub. Date: Dec. 15, 2016

(65) Prior Publication Data
US 2018/0170768 A1    Jun. 21, 2018

(30) Foreign Application Priority Data

Jun. 12, 2015 (KR) .................. 10-2015-0083473

(51) Int. Cl.
*C02F 1/00* (2006.01)
*C02F 1/44* (2006.01)
(Continued)

(52) U.S. Cl.
CPC ............... *C02F 1/003* (2013.01); *A61L 2/10* (2013.01); *B01D 35/16* (2013.01); *C02F 1/325* (2013.01);
(Continued)

(58) Field of Classification Search
CPC .............. C02F 1/003; C02F 2201/3222; C02F 2201/326; C02F 2303/14; C02F 2303/20;
(Continued)

(56) References Cited

U.S. PATENT DOCUMENTS 4,757,921 A * 7/1988 Snowball ................ C02F 9/005
210/259
2003/0132250 A1* 7/2003 Greene ..................... B67D 1/00
222/185.1

(Continued)

FOREIGN PATENT DOCUMENTS

EP     1 112 687 A2    7/2001
JP     2014189299 A  * 10/2014
(Continued)

OTHER PUBLICATIONS

Hamamoto ("New water disinfection system using UVA light-emitting diodes") May 8, 2007.*
Abstract of KR 10-2005-0111948-A published on Nov. 29, 2005.

*Primary Examiner* — Waqaas Ali
(74) *Attorney, Agent, or Firm* — Birch, Stewart, Kolasch & Birch, LLP (57) ABSTRACT

The present invention relates to a water purifier comprising a body having an external appearance of a shape able to hold water, and a discharge device which is located inside the body and discharges the water held in the body to the outside of the body; wherein the discharge device comprises a discharge unit body which has a hollow shape that provides a flow pathway for discharging the water held in the body, and a light-source unit which is disposed facing the discharge unit body and irradiates light having the wavelength band of ultraviolet light towards water flowing through the discharge unit body.

7 Claims, 8 Drawing Sheets

(51) Int. Cl.
 *C02F 1/32* (2006.01)
 *A61L 2/10* (2006.01)
 *B01D 35/16* (2006.01)

(52) U.S. Cl.
 CPC ........ *C02F 1/441* (2013.01); *C02F 2201/326* (2013.01); *C02F 2201/3222* (2013.01); *C02F 2303/04* (2013.01); *C02F 2303/14* (2013.01); *C02F 2303/20* (2013.01); *C02F 2307/10* (2013.01)

(58) Field of Classification Search
 CPC .. C02F 2303/04; C02F 2307/10; C02F 1/325; C02F 1/441; A61L 2/10; B01D 35/16
 See application file for complete search history.

(56) References Cited

U.S. PATENT DOCUMENTS

| | | |
|---|---|---|
| 2007/0163934 A1 | 7/2007 | Kim et al. |
| 2011/0215037 A1* | 9/2011 | Cassassuce ............ B01D 35/14 210/95 |
| 2015/0034545 A1 | 2/2015 | Park et al. |
| 2016/0046508 A1* | 2/2016 | Orita .................... B67D 1/0004 222/146.1 |

FOREIGN PATENT DOCUMENTS

| | | |
|---|---|---|
| KR | 10-2001-0058310 A | 7/2001 |
| KR | 20-0330424 Y1 | 10/2003 |
| KR | 10-2005-0111948 A | 11/2005 |
| KR | 10-2010-0131802 A | 12/2010 |
| KR | 10-2012-0037141 A | 4/2012 |
| KR | 10-2012-0045950 A | 5/2012 |
| KR | 10-2015-0050205 A | 5/2015 |

* cited by examiner

| UV Dose | 0 | 0.17 | 0.34 | 1.00 | 1.67 |
|---|---|---|---|---|---|
| Time (sec) | 0 | 30 | 60 | 180 | 300 |
| Colon Bacillus | 0% | 97.64% | 99.97% | >99.99% | >99.99% |
| Salmonella | 0% | 97.81% | 99.78% | >99.99% | >99.99% |
| Listeria | 0% | 59.57% | 88.25% | >99.97% | >99.99% |

WATER PURIFIER

CROSS REFERENCE TO RELATED APPLICATIONS

This application is the National Phase of PCT International Application No. PCT/KR2016/000092, filed on Jan. 6, 2016, which claims priority under 35 U.S.C. 119(a) to Patent Application No. 10-2015-0083473, filed in the Republic of Korea on Jun. 12, 2015, all of which are hereby expressly incorporated by reference into the present application.

TECHNICAL FIELD

Embodiments relate to a water purifier.

BACKGROUND ART

In general, a water purifier is an apparatus which purifies tap water, well water, stream water or river water into drinkable water satisfying a water quality standard using a physical, chemical or biological method or through combinations thereof. Most countries including Korea set water quality standards of drinkable water based on standards set by the World Health Organization (WHO), and, according to these standards, a water quality standard is set by multiplying a concentration of impurities in water, which is harmless to humans even if persons drink about 2 l of water a day for 70 years, by a safety factor and, thus, water satisfying the water quality standard of drinkable water may be considered as being safe.

As a water purifier is used in a home, an institution or an office, a discharge unit is stained with bacteria of hands and bacteria or dust suspended in the air and contacts food when water is poured through the discharge unit so as to make coffee or prepare instant cup noodles and, thus, a large amount of bacteria is inevitably present around the discharge unit.

Further, water is always collected around the discharge unit, through which water is discharged to the outside from the water purifier, and the discharge unit is exposed to the air and is thus in a state in which bacteria or germs are able to propagate.

In a conventional water purifier, a user must generally clean a discharge unit using a cotton swab or a toothbrush or frequently clean the discharge unit using hot water or vinegar.

However, it is not easy for the user to clean the discharge unit every day and, thus, bacteria may propagate within the discharge unit.

Thereby, although sterilization of a water storage unit of the water purifier or sterilization of a filter unit is carried out, if the discharge unit to discharge water is not clean, users may drink water including bacteria.

Further, even if, in order to prevent such a problem, an LED radiating ultraviolet light is provided, a light source unit of hundreds of mW is generally necessary to sterilize flowing water and thus energy efficiency is lowered.

In addition, humidity of an LED module is increased by flowing water of the discharge unit and, thus, performance of the LED may be lowered.

Moreover, ultraviolet light radiated by the LED may discolor the discharge unit.

DISCLOSURE

Technical Problem

Embodiments provide a water purifier having a light source unit module which radiates ultraviolet light so as to prevent propagation of bacteria in a discharge unit.

Further, embodiments provide a water purifier having a light source unit module which sterilizes flowing water while preventing lowering of energy efficiency.

Further, embodiments provide a water purifier having a light source unit module which prevents lowering of performance of an LED due to increase in humidity of an LED module caused by flowing water in a discharge unit.

Moreover, embodiments provide a water purifier which prevents discoloration of a discharge unit by ultraviolet light radiated by an LED.

Technical Solution

In one embodiment, a water purifier includes a body having an external appearance of a shape able to hold water, and a discharge device located inside the body and discharging the water held in the body to the outside of the body, wherein the discharge device includes a discharge unit body having a hollow shape providing a flow path for discharging the water held in the body, and a light source unit disposed opposite the discharge unit body and radiating light having an ultraviolet wavelength band towards water flowing in the discharge unit body.

The light source unit may include a light emitting device configured to radiate the light, and a waterproof part disposed on an outer circumferential surface of the light emitting device and isolating the light emitting device from the water flowing in the discharge unit body.

The waterproof part may include Teflon having a light transmissive property.

The waterproof part may include quartz having a light transmissive property.

The discharge unit body may include a UV stabilizer.

The UV stabilizer may include a hindered amine light stabilizer (HALS).

The discharge unit body may include a UV resistant additive.

The UV resistant additive may be one of carbon black (C), titanium dioxide ($TiO_2$) and benzotriazole ($C_6H_5N_3$).

Advantageous Effects

Embodiments provide a water purifier having a light source unit module which radiates ultraviolet light so as to prevent propagation of bacteria in a discharge unit.

Further, embodiments provide a water purifier having a light source unit module which sterilizes flowing water while preventing lowering of energy efficiency.

Further, embodiments provide a water purifier having a light source unit module which prevents lowering of performance of an LED due to increase in humidity of an LED module caused by flowing water in a discharge unit.

Moreover, embodiments provide a water purifier which prevents discoloration of a discharge unit by ultraviolet light radiated by an LED.

BEST MODE

Hereinafter, embodiments will be apparently described with reference to the annexed drawings and description. However, the embodiments set forth herein may be variously modified, and it should be understood that there is no intent to limit the disclosure to the particular forms disclosed, but on the contrary, the embodiments are to cover all modifications, equivalents, and alternatives falling within the spirit and scope of the disclosure as defined by the claims. The embodiments are provided to more completely describe the disclosure to those skilled in the art.

In the following description of the embodiments, it will be understood that, when each element is referred to as being formed "on" or "under" another element, it can be directly "on" or "under" the other element or be indirectly formed with one or more intervening elements therebetween. Further, when an element is referred to as being formed "on" or "under" another element, not only the upward direction of the former element but also the downward direction of the former element may be included.

In addition, it will be understood that, although the relational terms "first", "second", "upper", "lower", etc. may be used herein to describe various elements, these terms neither require nor connote any physical or logical relations between substances or elements or the order thereof, and are used only to discriminate one substance or element from other substances or elements.

Thicknesses or sizes of respective layers in the drawings may be exaggerated, omitted or schematically illustrated for convenience and clarity of description. Further, sizes of respective elements may not fully represent actual sizes thereof.

Figure 1:
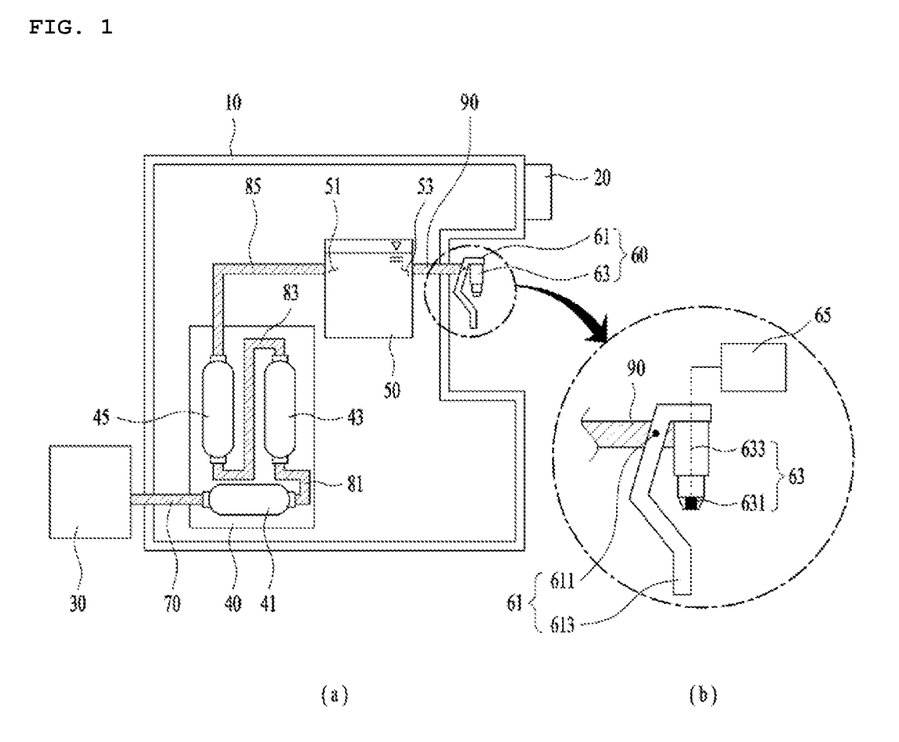
FIG. 1 is a view illustrating a water purifier in accordance with one embodiment.

FIG. 1 is a view illustrating a water purifier in accordance with one embodiment.

With reference to FIG. 1, a water purifier in accordance with one embodiment may include a water source 30 provided to supply water to the inside of the water purifier, a filter unit 40 provided to filter out contaminants and foreign substances from water supplied from the water source 30, a water storage unit 50 to store water, and a discharge device 60 provided to discharge water stored in the water storage unit 50 to the outside of the water purifier.

The discharge device 60 may include a discharge valve 61 provided to adjust an amount of water discharged to the outside, a discharge unit 63 provided to form a flow path for discharging water, and an LED control unit 65 to control a light source unit 631 provided on the inner surface of the discharge unit 63.

The discharge valve 61 may be provided such that, when a user presses the discharge valve 61 using a container to receive water, the discharge unit 63 discharges water, and the discharge valve 61 may include a pressing part 613 providing a space pressed by the user using the container and a pivot part 611 provided to pivot the pressing part 613 using applied force and thus to open or close the discharge valve 61.

The discharge unit 63 may include a light source unit 631 to irradiate water flowing in the discharge unit 63 with ultraviolet light to sterilize the water, and a discharge unit body 633 to provide a water flow path.

The light source unit 631 may include an LED 6311 provided to radiate ultraviolet light, and a waterproof film 6313 provided on the outer circumferential surface of the LED 6311 to protect the LED 6311 from water.

The water source 30 may be a tank which stores unpurified raw water, or be a water pipe connecting a water supply source to the inside of a building. In this embodiment, the filter unit 40 may include a first filter 41 to remove impurities having a large particle size, such as rust, soil, sand, etc., a second filter 43 to remove heavy metals, phenol, bacteria, etc. through reverse osmosis, and a third filter 45 to finally purify water.

However, the number and functions of filters of the filter unit 40 may be different according to user needs and are not limited to the description of this embodiment as long as the filters may have a function of purifying water of the water source 30.

The LED control unit 65 may control an operating time and an operating cycle of the LED 6311 of the light source unit 631, an intensity of light radiated by the LED 6311, etc.

A connection wire may be provided between the LED control unit 65 and the LED 6311, as exemplarily shown in this figure, or the LED control unit 65 may be directly connected to the LED 6311 without a connection wire.

When a user opens the discharge unit 63, water may be discharged to the outside of the water purifier. Although only one discharge unit 63 may be provided, two discharge units 63, i.e., a discharge unit 63 for cold water and a discharge unit 63 for hot water, may be generally provided, or three or more discharge units 63 may be provided.

The water purifier in accordance with this embodiment may include a water supply duct 70 providing a flow path of water from the water source 30 to the filter unit 40, a filter duct unit 81, 83 and 85 providing flow paths of water within the filter unit 40, and a discharge duct 90 providing a flow path of water from the water storage unit 50 to the discharge unit 60.

The filter duct unit 80 may include a first filter duct 81 providing a flow path of water from the first filter 41 to the second filter 43, a second filter duct 83 providing a flow path of water from the second filter 43 to the third filter 45, and a third filter duct 85 providing a flow path of water from the third filter 45 to the water storage unit 50.

Figure 2:
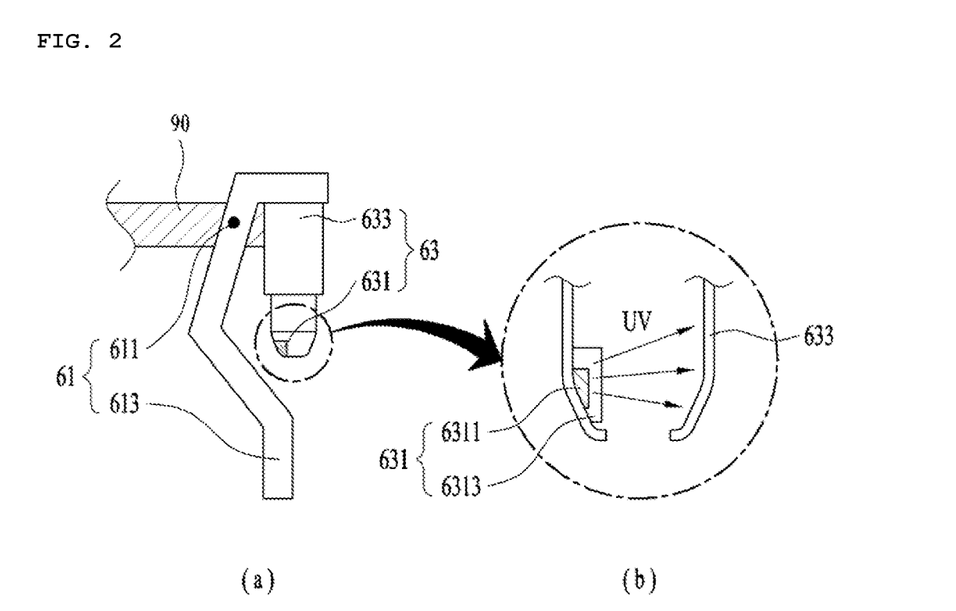
FIG. 2 is a view illustrating a light source unit provided in a discharge unit of the water purifier in accordance with the embodiment.

FIG. 2 is a view illustrating the light source unit provided in the discharge unit 63 of the water purifier in accordance with the embodiment.

With reference to FIG. 2, the light source unit 631 may be provided on the inner surface of the discharge unit body 633.

The discharge unit body 633 may have a hollow shape to provide a flow path for discharging water from the inside of the water purifier to the outside of the water purifier, as described above, and the light source unit 631 may be provided on the inner surface of the discharge unit body 633 and radiate ultraviolet light towards water flowing in the discharge unit body 633.

In order to irradiate water flowing in the discharge unit 63 with ultraviolet light, a mercury lamp (not shown) is generally provided. However, the mercury lamp (not shown) has a restrictive spectrum of radiated ultraviolet light, a lower on/off speed than the light source unit 631 and lower energy efficiency than the light source unit 631.

Ultraviolet light may be divided into three kinds UVA, UVB and UVC according to wavelength.

UVA is ultraviolet light having a wavelength band of 320 nm to 400 nm, UVB is ultraviolet light having a wavelength band of 290 nm to 320 nm, and UVC is ultraviolet light having a wavelength band of 290 nm or less.

A spectrum of ultraviolet light radiated by the mercury lamp is limited to a designated range, but the LED 6311 of the light source unit 63 in accordance with this embodiment may employ different spectrums of radiated ultraviolet light according to user requirements.

UVA has excellent sterilizing effects, and UVB and UVC are harmful to humans.

The conventional mercury lamp cannot adjust a wavelength band of radiated ultraviolet light and may thus radiate not only UVA for sterilization but also UVB and UVC, which are harmful to humans.

However, the light source unit 631 in accordance with this embodiment radiates ultraviolet light using the LED 6311 and may thus mainly radiate UVA except for UVB and UVC, which are harmful to humans, thus providing a sterilization device which has improved sterilizing ability and is harmless to humans.

However, the light source unit 631 in accordance with this embodiment may selectively radiate UVA, UVB and UVC, as needed, but is not limited thereto.

Figure 8:
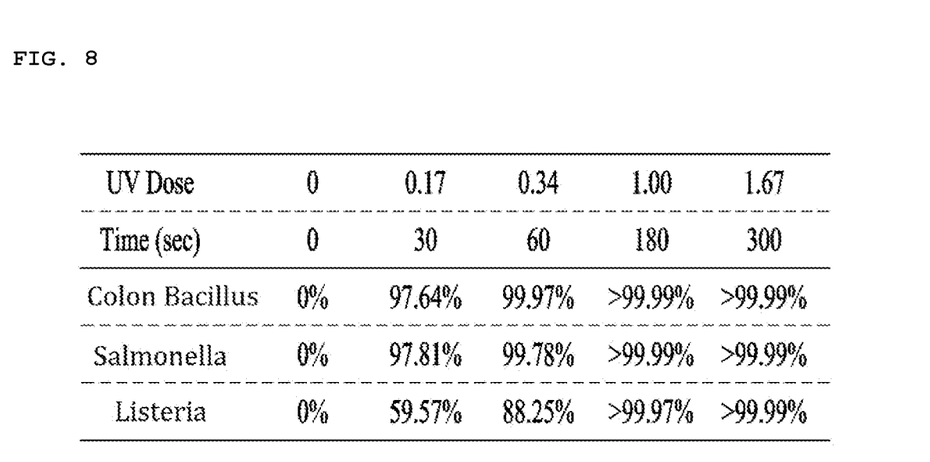
FIG. 8 is a table representing sterilizing abilities of colon bacillus, salmonella and listeria according to doses of ultraviolet light per area (mJ/cm$^2$).

FIG. 8 is a table representing sterilizing abilities of colon *bacillus*, *salmonella* and *listeria* according to doses of ultraviolet light per area (mJ/cm$^2$).

When colon *bacillus* is irradiated with ultraviolet light radiated by the LED 6311 of the light source unit 631 for about 30 seconds, 97.64% of the colon *bacillus* is killed and, when colon *bacillus* is irradiated with the ultraviolet light for about 60 seconds, most, i.e., 99.97%, of the colon *bacillus* is killed.

Further, when *salmonella* is irradiated with ultraviolet light radiated by the LED 6311 of the light source unit 631 for about 30 seconds, 97.81% of the *salmonella* is killed and, when *salmonella* is irradiated with the ultraviolet light for about 60 seconds, most, i.e., 99.78%, of the *salmonella* is killed.

Moreover, when *listeria* is irradiated with ultraviolet light radiated by the LED 6311 of the light source unit 631 for about 30 seconds, 59.67% of the *listeria* is killed, when *listeria* is irradiated with the ultraviolet light for about 60 seconds, 88.25% of the *listeria* is killed and, when *listeria* is irradiated with the ultraviolet light for about 180 seconds, most, i.e., 99.97%, of the *listeria* is killed.

Therefore, when the light source unit 631 in accordance with this embodiment radiates ultraviolet light for about 60 seconds, most colon *bacillus* and *salmonella* are killed and, when the light source unit 631 radiates ultraviolet light for about 180 seconds, most *listeria* is killed.

Therefore, if the discharge unit 63 of this embodiment is provided with the light source unit 631, water discharged from the inside of the water purifier may be irradiated with ultraviolet light using a smaller amount of energy.

As described above, the lights source unit 631 may further include the waterproof part 6313 provided as a waterproof film disposed on the outer circumferential surface of the light source unit 631.

The light source unit 631 is disposed on the inner circumferential surface of the discharge unit 63 in which water always flows and, thus, if the waterproof part 6313 is not provided, humidity in the light source unit 631 is raised due to water and thereby an LED chip (not shown) is damaged and thus not normally operated.

Figure 7:
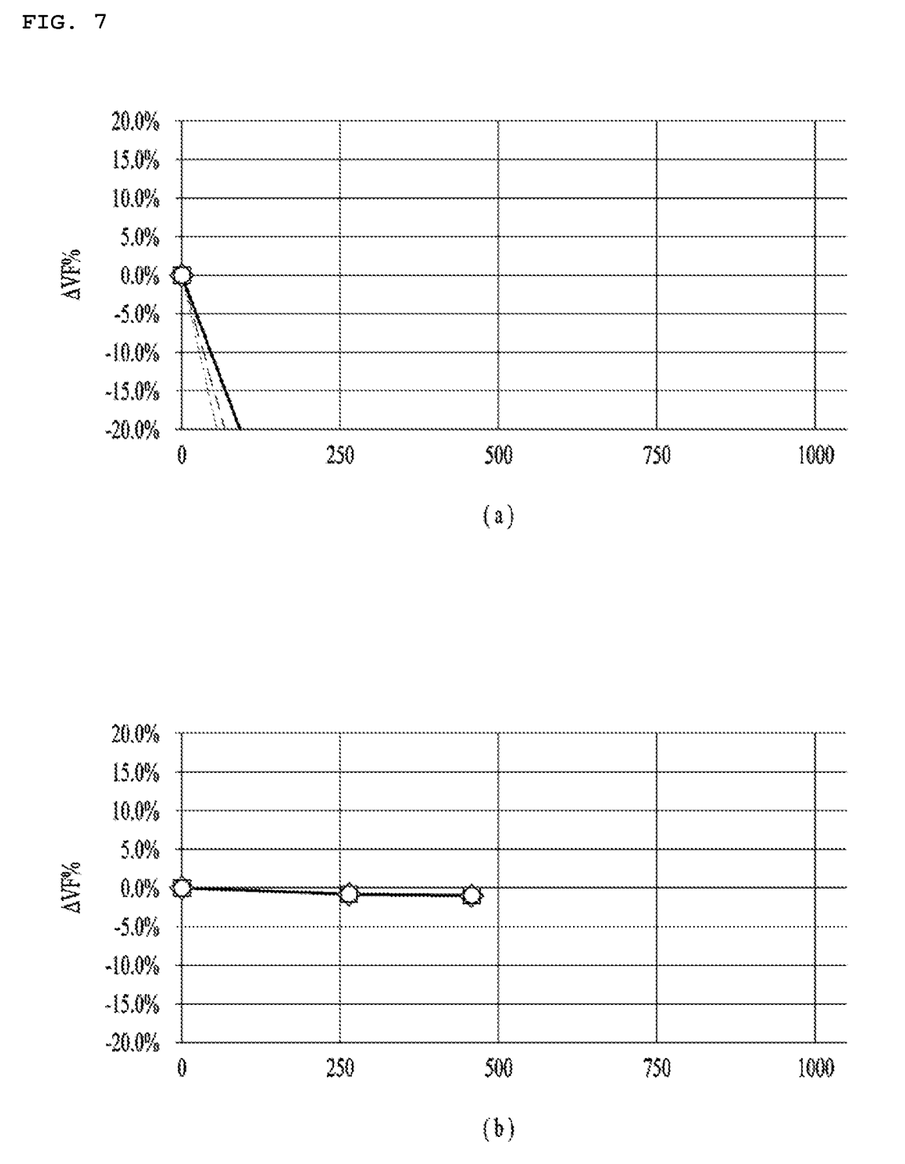
FIG. 7 illustrates graphs representing variations in voltage forward (VF) according to operating times of an LED chip which is exposed to moisture and thus damaged (not shown) and a waterproofed LED chip (not shown).

FIG. 7 illustrates graphs representing variations in voltage forward (VF) according to operating times of an LED chip which is exposed to moisture and thus damaged (not shown) and a waterproofed LED chip (not shown).

In more detail, FIG. 7(*a*) is a graph representing variation in voltage forward (VF) according to an operating time of the LED chip which is exposed to moisture and thus damaged (not shown), and FIG. 7(*b*) is a graph representing variation in voltage forward (VF) according to an operating time of the waterproofed LED chip (not shown).

Here, the horizontal axis indicates a time for which current is supplied to the LED chip (not shown), and the vertical axis indicates variation in voltage forward (VF) according to time.

Figure 6:
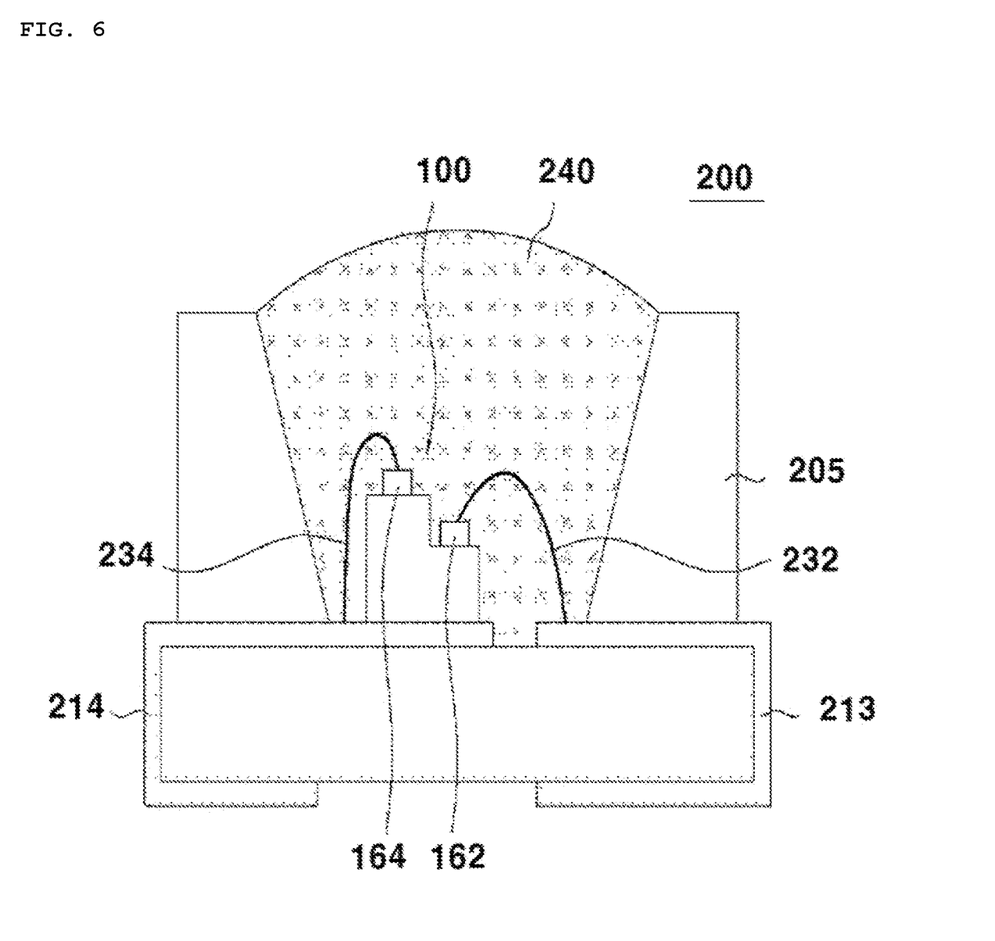
FIG. 6 is a cross-sectional view of a light emitting device package of the water purifier in accordance with the embodiment.

An intensity of light radiated by an LED chip (not shown) is varied according to voltage forward (VF) and, if current is supplied for about 456 hr, a voltage forward (VF) value of the LED chip (not shown) exposed to moisture and thus damaged, as exemplarily shown in FIG. 6, is lowered by 95.6% but a voltage forward (VF) value of the waterproofed LED chip (not shown) is lowered by 0.8%.

That is, the LED chip (not shown) in accordance with this embodiment is waterproofed and, thus, the LED chip (not show) may be operated for a long time.

That is, the water purifier in accordance with this embodiment may further include the waterproof part 6313 to protect the outer circumferential surface of the light source unit 631 from moisture due to water.

The waterproof part 6313 is formed of a material which may isolate the light source unit 631 from water and transmit ultraviolet light radiated by the light source unit 631.

Therefore, the waterproof part 6313 may be formed of Teflon or quartz which may transmit ultraviolet light.

Figure 3:
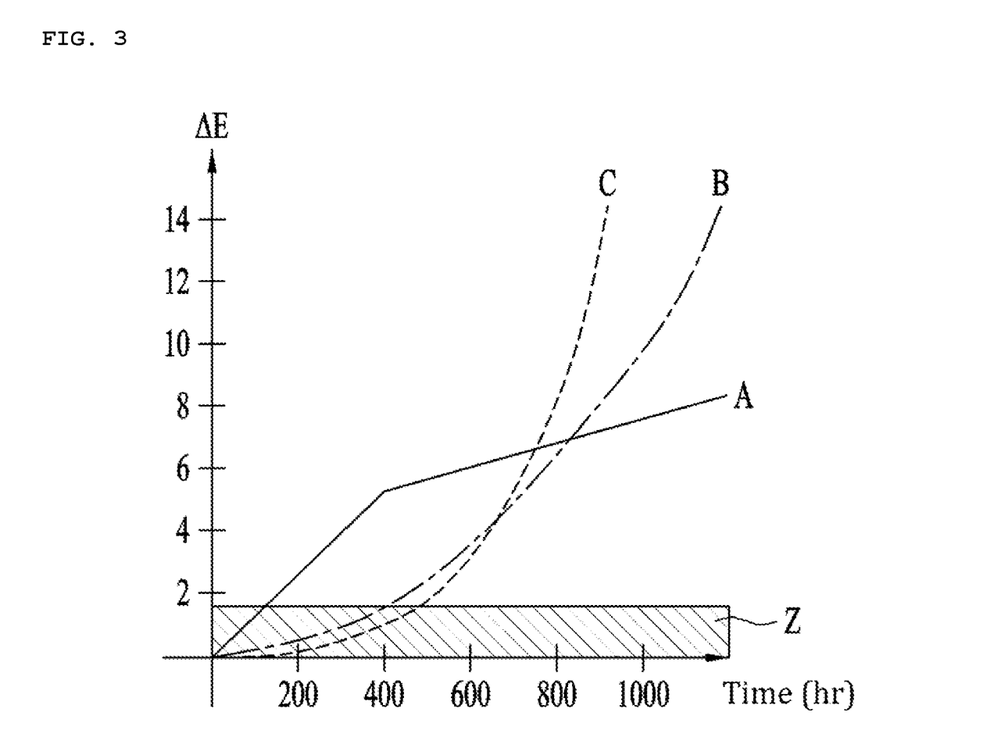
FIG. 3 is a graph representing a discoloration degree of the discharge unit of the water purifier in accordance with the embodiment according to a material of the discharge unit and an ultraviolet light exposure time of the discharge unit.

FIG. 3 is a graph representing a discoloration degree of the discharge unit of the water purifier in accordance with the embodiment according to a material of the discharge unit and an ultraviolet light exposure time of the discharge unit.

In the graph, the horizontal axis indicates an irradiation time of ultraviolet light and the vertical axis indicates a discoloration degree according to a predetermined standard.

Further, an area Z shown by slashes in the graph is an area representing an allowable discoloration degree range.

With reference to FIG. 3, it may be understood that, if discharge units 63 formed of polypropylene (PP), high impact polystyrene (HIPS) and acrylonitrile butadiene styrene (ABS) are exposed to ultraviolet light, the discharge unit 63 formed of polypropylene (PP) (shown by line A) is most rapidly discolored and the discharge unit 63 formed of high impact polystyrene (HIPS) (shown by line B) and the discharge unit 63 formed of acrylonitrile butadiene styrene (ABS) (shown by line C) are sequentially discolored.

Therefore, the discharge unit 63 in accordance with this embodiment may be formed of acrylonitrile butadiene styrene (ABS) (shown by line C).

However, since, if the discharge unit 60 is irradiated with ultraviolet light for 500 hours or more, the discoloration degree of the discharge unit 60 also deviates from the predetermined area Z, the discharge unit 60 may further include a UV resistant additive and a UV stabilizer.

If the discharge unit 63 includes a UV resistant additive and a UV stabilizer, a discoloration degree of the discharge unit 63 by ultraviolet light radiated by the light source unit 631 is lowered.

In more detail, the UV resistant additive added to the discharge unit 63 in accordance with this embodiment may be carbon black (C), titanium dioxide ($TiO_2$) or benzotriazole ($C_6H_5N_3$).

Further, the UV stabilizer added to the discharge unit 63 in accordance with this embodiment may be a hindered amine light stabilizer (HALS).

However, the disclosure is not limited to the above-described UV resistant additives and UV stabilizers in this embodiment, and other materials, which may lower the discoloration degree of the discharge unit 60 by ultraviolet light, may be used.

Figure 4:
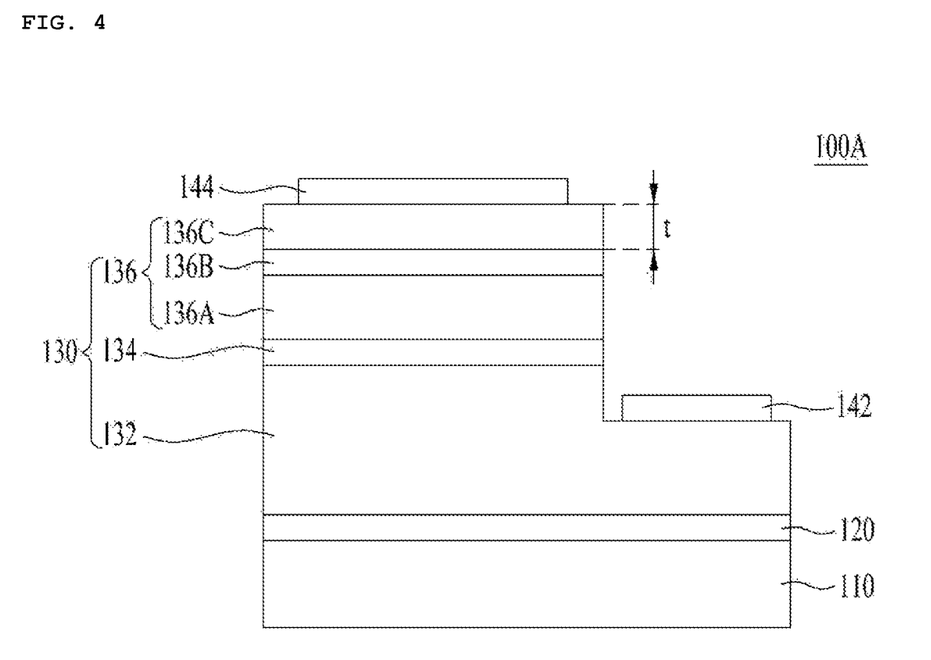
FIG. 4 is a cross-sectional view illustrating a light emitting device.

FIG. 4 is a cross-sectional view illustrating a light emitting device.

A light emitting device 100A shown in FIG. 4 includes a substrate 110, a buffer layer 120, a light emitting structure 130, and first and second electrodes 142 and 144.

The substrate 110 may include a conductive material or a non-conductive material. For example, the substrate 110 may include at least one of sapphire ($Al_2O_3$), GaN, SiC, ZnO, GaP, InP, $Ga_2O_3$, GaAs or Si.

In order to reduce lattice mismatch and a difference in coefficients of thermal expansion between the substrate 110 and the light emitting structure 130, the buffer layer (or a transition layer) 120 may be disposed between the substrate 110 and the light emitting structure 130. The buffer layer 120 may include, for example, at least one selected from the group consisting of Al, In, N and Ga, without being limited thereto. Further, the buffer layer 120 may have a monolayer or multilayer structure.

The light emitting structure 130 includes a first conductivity-type semiconductor layer 132, an active layer 134 and a second conductivity-type semiconductor layer 136, sequentially disposed on the buffer layer 120.

The first conductivity-type semiconductor layer 132 may be disposed on the buffer layer 120 and be formed of a group III-V or group II-VI compound semiconductor doped with a first conductivity-type dopant. If the first conductivity-type semiconductor layer 132 is an n-type semiconductor layer, the first conductivity-type dopant may be an n-type dopant including Si, Ge, Sn, Se and Te, but is not limited thereto.

For example, the first conductivity-type semiconductor layer 132 may include a semiconductor material having an empirical formula of $Al_xIn_yGa_{(1-x-y)}N$ ($0 \leq x \leq 1$, $0 \leq y \leq 1$, $0 \leq x+y \leq 1$). The first conductivity-type semiconductor layer 132 may include at least one selected from the group consisting of GaN, InN, AlN, InGaN, AlGaN, InAlGaN, AlInN, AlGaAs, InGaAs, AlInGaAs, GaP, AlGaP, InGaP, AlInGaP and InP.

The active layer 134 is disposed on the first conductivity-type semiconductor layer 132 and emits light having energy determined by an intrinsic energy band of a material forming the active layer 134 through combination of electrons (or holes) injected through the first conductivity-type semiconductor layer 132 and holes (or electrons) injected through the second conductivity-type semiconductor layer 136. The active layer 134 may have at least one of a double hetero structure, a multi-well structure, a single quantum well structure, a multi-quantum well (MQW) structure, a quantum-wire structure or a quantum dot structure.

Well/barrier layers of the active layer 134 may be formed to have at least one paired structure selected from the group consisting of InGaN/GaN, InGaN/InGaN, GaN/AlGaN, InAlGaN/GaN, GaAs(InGaAs)/AlGaAs and GaP(InGaP)/AlGaP, but is not limited thereto. The well layer may be formed of a material having lower bandgap energy than the bandgap energy of the barrier layer.

A conductive clad layer (not shown) may be formed on and/or under the active layer 134. The conductive clad layer (not shown) may be formed of a semiconductor having higher bandgap energy than the bandgap energy of the barrier layer of the active layer 134. For example, the conductive clad layer may include GaN, AlGaN, InAlGaN or a superlattice structure. Further, the conductive clad layer may be doped with an n-type or p-type dopant.

In accordance with this embodiment, the active layer 134 emits light of an ultraviolet wavelength band. Here, the ultraviolet wavelength band means a wavelength band of 100 nm to 400 nm. Particularly, the active layer 134 may emit light of a wavelength band of 100 nm to 280 nm.

The second conductivity-type semiconductor layer 136 may be disposed on the active layer 134 and be formed of a compound semiconductor, i.e., a group III-V or group II-VI compound semiconductor. For example, the second conductivity-type semiconductor layer 136 may be formed of a semiconductor material having an empirical formula of $In_xAl_yGa_{1-x-y}N$ The second conductivity-type semiconductor layer 136 may be doped with a second conductivity-type dopant. If the second conductivity-type semiconductor layer 136 is a p-type semiconductor layer, the second conductivity-type dopant may be a p-type dopant including Mg, Zn, Ca, Sr and Ba.

The first conductivity-type semiconductor layer 132 may be implemented as an n-type semiconductor layer, and the second conductivity-type semiconductor layer 136 may be implemented as a p-type semiconductor layer. Otherwise, the first conductivity-type semiconductor layer 132 may be implemented as a p-type semiconductor layer, and the second conductivity-type semiconductor layer 136 may be implemented as an n-type semiconductor layer.

The light emitting structure 130 may be implemented as one of an N-P junction structure, a P-N junction structure, an N-P-N junction structure and a P-N-P junction structure.

In accordance with this embodiment, if the active layer 134 emits light of an ultraviolet wavelength band, as described above, the second conductivity-type semiconductor layer 136 may include a second conductivity-type first semiconductor layer 136A and a second conductivity-type second semiconductor layer 136C.

The second conductivity-type first semiconductor layer 136A is disposed on the active layer 134. Each of the second conductivity-type first semiconductor layer 136A and the first conductivity-type semiconductor layer 132 may include AlGaN. The reason for this is that AlGaN absorbs a smaller amount of light of the ultraviolet wavelength band than GaN or InAlGaN.

The second conductivity-type second semiconductor layer 136C is disposed on the second conductivity-type first semiconductor layer 136A. The second conductivity-type second semiconductor layer 136C serves to effectively supply holes from the second electrode 144 to the active layer 134 to improve electrical characteristics of the light emitting device 100A. For example, the second conductivity-type second semiconductor layer 136B may include GaN or InAlGaN.

If the first conductivity-type is an n-type and the second conductivity-type is a p-type, the second conductivity-type first semiconductor layer 136A may function as an electron blocking layer (EBL). Further, the second conductivity-type first semiconductor layer 136A functioning as the EBL layer may have an AlGaN/AlGaN superlattice structure or an AlGaN bulk layer.

In order to allow the second conductivity-type first semiconductor layer 136A to transmit light emitted by the active layer 134, the energy bandgap of the second conductivity-type first semiconductor layer 136A may be greater than the energy bandgap of the active layer 134. For this purpose, although varied according to the wavelength of light emitted by the active layer 134, a content ratio of aluminum in the second conductivity-type first semiconductor layer 136A may be 0.3 or more.

Further, the second conductivity-type semiconductor layer 136 may further include a second conductivity-type third semiconductor layer 136B. The second conductivity-type third semiconductor layer 136B may be disposed between the second conductivity-type first semiconductor layer 136A and the second conductivity-type second semiconductor layer 136C. For example, the second conductivity-type third semiconductor layer 136B may include at least one AlGaN layer. Here, if the second conductivity-type third semiconductor layer 136B includes a plurality of AlGaN layers, aluminum concentrations of the AlGaN layers may have a gradient or be modulated.

The first electrode 142 is disposed on the first conductivity-type semiconductor layer 132 exposed by Mesa etching. The first electrode 142 may include a material being in ohmic contact and serve as an ohmic layer and, thus, it is not necessary to separately dispose an ohmic layer, or a separate ohmic layer may be disposed under the first electrode 142.

The second electrode 144 may be disposed on the second conductivity-type second semiconductor layer 136C. The first and second electrodes 142 and 144 may be formed of materials which may reflect or transmit light emitted by the active layer 134 without absorption and be grown on the first and second conductivity-type semiconductor layers 132 and 136 with high quality. For example, the first and second electrodes 142 and 144 may be respectively formed of metals selected from the group consisting of Ag, Ni, Al, Rh, Pd, Ir, Ru, Mg, Zn, Pt, Au, Hf and selective combinations thereof.

Particularly, the second electrode 144 may be a transparent conductive oxide (TCO). For example, the second electrode 144 may include at least one selected from the group consisting of the above-described metals, indium tin oxide (ITO), indium zinc oxide (IZO), indium zinc tin oxide (IZTO), indium aluminum zinc oxide (IAZO), indium gallium zinc oxide (IGZO), indium gallium tin oxide (IGTO), aluminum zinc oxide (AZO), antimony tin oxide (ATO), gallium zinc oxide (GZO), IrOx, RuOx, RuOx/ITO, Ni/IrOx/Au and Ni/IrOx/Au/ITO, but is not limited thereto. The second electrode 144 may include a material being in ohmic contact with a second conductivity-type GaN layer 126C.

Further, the second electrode 144 may be formed to have a monolayer or multilayer structure using a reflective electrode material having ohmic characteristics. If the second electrode 144 may function as an ohmic layer, a separate ohmic layer (not shown) need not be formed.

Figure 5:
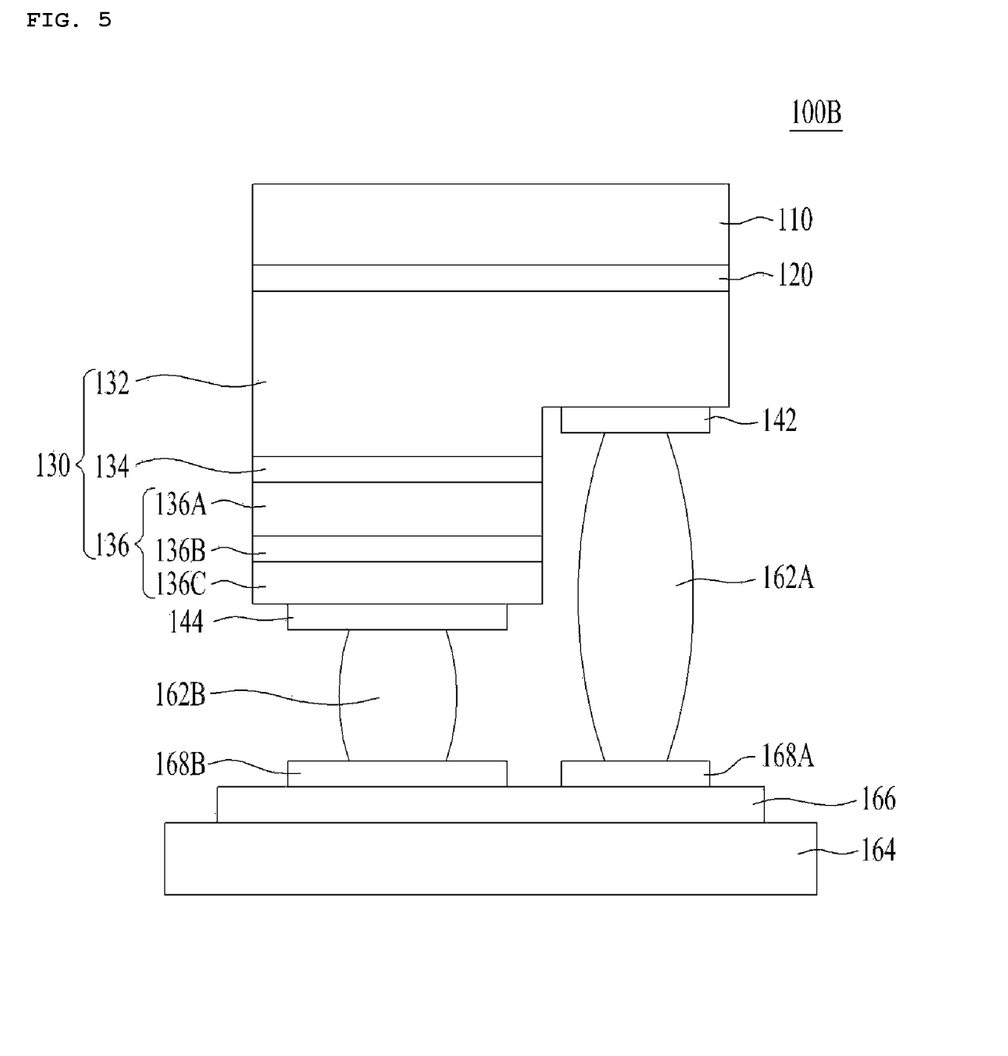
FIG. 5 is a cross-sectional view illustrating a light emitting device provided in a light source unit module of the water purifier in accordance with the embodiment.

FIG. 5 is a cross-sectional view illustrating a light emitting device provided in the light source unit module of the water purifier in accordance with the embodiment.

The light emitting device 100A exemplarily shown in FIG. 4 has a horizontal structure and, thus, light emitted by the active layer 134 is emitted through the second conductivity-type semiconductor layer 136 and the second electrode 144. For this purpose, the second conductivity-type semiconductor layer 136 and the second electrode 144 may be formed of light transmissive materials, and the first conductivity-type semiconductor layer 132, the buffer layer 120 and the substrate 110 may be formed of light transmissive or light non-transmissive materials.

However, a light emitting device exemplarily shown in FIG. 5 has a flip-chip bonding structure and, thus, light emitted by an active layer 134 is emitted through a substrate 110, a buffer layer 120 and a first conductivity-type semiconductor layer 132. For this purpose, the substrate 110, the buffer layer 120 and the first conductivity-type semiconductor layer 132 may be formed of light transmissive materials, and a second conductivity-type semiconductor layer 136 and a second electrode 144 may be formed of light transmissive or light non-transmissive materials.

Further, differently from the light emitting device 100A exemplarily shown in FIG. 4, the light emitting device exemplarily shown in FIG. 5 having the flip-chip bonding structure further includes first and second bumps 162A and 162B, a submount 164, a protective layer 166 and first and second metal layers (or metal pads) 168A and 168B. Since the light emitting device 100B exemplarily shown in FIG. 5 is the same as the light emitting device 100A exemplarily shown in FIG. 4 except for such differences, parts of the light emitting device 100B which are substantially the same as those of the light emitting device 100A are denoted by the same reference numerals even though they are depicted in different drawings and a detailed description thereof will thus be omitted.

The submount 164 may be a semiconductor substrate formed of, for example, AlN, BN, silicon carbide (SiC), GaN, GaAs, Si, etc., without being limited thereto, or formed of a semiconductor material having excellent thermal conductivity. Further, the submount 164 may include a device for preventing electro static discharge (ESD) formed as a Zener diode.

The first and second metal layers 168A and 168B are arranged on the submount 164 so as to be spaced apart from each other in the horizontal direction. The first bump 162A may be disposed between the first metal layer 168A and the first electrode 142, and the second bump 162B may be disposed between the second metal layer 168B and the second electrode 144.

The first electrode 142 is connected to the first metal layer 168A of the submount 164 through the first bump 162A, and the second electrode 144 is connected to the second metal layer 168B of the submount 164 through the second bump 162B.

Although not shown in the drawings, a first upper bump metal layer (not shown) may be further disposed between the first electrode 142 and the first bump 162A, and a first lower bump metal layer (not shown) may be further disposed between the first metal layer 168A and the first bump 162A. Here, the first upper bump metal layer and the first lower bump metal layer serve to mark a position where the first bump 162A will be located. Similarly, a second upper bump metal layer (not shown) may be further disposed between the second electrode 144 and the second bump 162B, and a second lower bump metal layer (not shown)

may be further disposed between the second metal layer 168B and the second bump 162B. Here, the second upper bump metal layer and the second lower bump metal layer serve to mark a position where the second bump 162B will be located.

If the submount 164 is formed of a material having electrical conductivity, such as Si, the protective layer 166 may be disposed between the first and second metal layers 168A and 168B and the submount 164, as exemplarily shown in FIG. 5. Here, the protective layer 166 may be formed of an insulating material.

FIG. 6 is a cross-sectional view of a light emitting device package of the water purifier in accordance with the embodiment.

With reference to FIG. 6, a light emitting device package 200 includes a package body 205, first and second lead frames 213 and 214 installed on the package body 205, a light emitting device 100 arranged in the package body 205 and conductively connected to the first and second lead frames 213 and 214, a molding member 240 surrounding the light emitting device 100, and first and second wires 232 and 234.

The package body 205 may include silicone, a synthetic resin or a metal, and an inclined surface may be formed around the light emitting device 100.

The first and second lead frames 213 and 214 are electrically isolated from each other and serve to provide power to the light emitting device 100. Further, the first and second lead frames 213 and 214 may serve to reflect light generated by the light emitting device 100 to increase luminous efficacy, and serve to discharge heat generated by the light emitting device 100 to the outside.

The light emitting device 100 may be arranged on the second lead frame 214, as exemplarily shown in this figure, but is not limited thereto. For example, differently from FIG. 10, the light emitting device 100 may be arranged on the first lead frame 213 or arranged on the package body 205.

The light emitting device 100 may be conductively connected to the first and second lead frames 213 and 214 through any one of a wire bonding method, a flip-chip bonding method or a die-bonding method. The first electrode 162 of the light emitting device 100 exemplarily shown in FIG. 10 may be conductively connected to the first lead frame 213 through the first wire 232 and the second electrode 164 may be conductively connected to the second lead frame 214 through the second wire 234, but the embodiment is not limited thereto.

The molding member 240 may surround the light emitting device 100 and thus protect the light emitting device 100. Further, the molding member 240 may include phosphors and thus change the wavelength of light emitted by the light emitting device 100.

Further, the light emitting device package may function as a light source unit to radiate light having an ultraviolet wavelength band in the water purifier in accordance with this embodiment.

INDUSTRIAL APPLICABILITY

A water purifier in accordance with one embodiment includes a light source module to radiate ultraviolet light and may thus sterilize flowing water and increase energy efficiency.

The invention claimed is:

1. A water purifier comprising:
   a water source;
   a filter unit provided to filter out contaminants and foreign substances from water supplied from the water source;
   a water storage unit; and
   a discharge device provided to discharge water stored in the water storage unit to the outside of the water purifier,
   wherein the discharge device comprises:
      a discharge valve provided to adjust an amount of water being discharged to the outside of the water purifier;
      a discharge unit forming a flow path for discharging water and having a light source unit positioned within the flow path; and
      an LED (light emitting device) control unit provided to control the light source unit,
      wherein the light source unit comprises:
      an LED provided to radiate ultraviolet light; and
         a waterproof part provided on an outer circumferential surface of the LED to protect the LED from water,
      wherein the discharge unit further comprises a discharge unit body having a hollow shape to provide the flow path for discharging water from inside of the water purifier to outside of the water purifier,
      wherein the light source unit is provided on an inner surface of the discharge unit body and radiates ultraviolet light towards water flowing in the discharge unit body,
      wherein the waterproof part transmits the ultraviolet (UV) light radiated by the LED,
      wherein the discharge unit includes a UV resistant additive and a UV stabilizer,
      wherein the LED control unit controls an operating time and an operating cycle of the LED and an intensity of light radiated by the LED, and
      wherein an irradiation time of the LED is greater than 180 seconds.

2. The water purifier according to claim 1, wherein the UV light does not include UVB and UVC.

3. The water purifier according to claim 1, wherein the waterproof part is formed of quartz.

4. The water purifier according to claim 1, wherein the discharge unit is formed of acrylonitrile butadiene styrene (ABS).

5. The water purifier according to claim 1, wherein the UV resistant additive is one of carbon black (C), titanium dioxide ($TiO_2$) and benzotriazole ($C_6H_5N_3$).

6. The water purifier according to claim 5, wherein the UV stabilizer is a hindered amine light stabilizer (HALS).

7. The water purifier according to claim 1, wherein the LED has a flip-chip bonding structure.

* * * * *